United States Patent
Yang et al.

(10) Patent No.: US 9,857,314 B1
(45) Date of Patent: Jan. 2, 2018

(54) QUALITY DETECTING DEVICE AND METHOD

(71) Applicant: Industrial Technology Research Institute, Hsinchu (TW)

(72) Inventors: Fu-Cheng Yang, Hsinchu (TW); Chia-Liang Yeh, Hsinchu (TW); Wei-Hsiung Tsai, Hsinchu (TW); Keng-Li Lin, Hsinchu (TW); Yeou-Sung Lin, Hsinchu (TW); Mao-Sheng Huang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/392,713

(22) Filed: Dec. 28, 2016

(30) Foreign Application Priority Data

Nov. 18, 2016 (TW) .............................. 105137828 A

(51) Int. Cl.
*G01J 3/00* (2006.01)
*G01N 21/958* (2006.01)
(Continued)

(52) U.S. Cl.
CPC ....... *G01N 21/958* (2013.01); *G01N 21/4788* (2013.01); *G01N 2021/9513* (2013.01)

(58) Field of Classification Search
CPC .. G01N 21/958; G01N 21/4788; G01N 21/47; G01N 21/31; G01N 21/55; G01J 3/02; G01J 3/28; G01J 3/42
See application file for complete search history.

(56) References Cited

U.S. PATENT DOCUMENTS

| 6,933,185 B2 | 8/2005 | Wada et al. |
| 7,184,132 B2 | 2/2007 | Tsao |
(Continued)

FOREIGN PATENT DOCUMENTS

| CN | 102192908 A | 9/2011 |
| CN | 102543789 A | 7/2012 |
(Continued)

OTHER PUBLICATIONS

Excimer-Laser Annealing Microstructure Evolution and a Novel Characterization Technique, Paul C. van der Wilt, SID 2014 Digest, 2014, 149-152.

*Primary Examiner* — Abdullahi Nur
(74) *Attorney, Agent, or Firm* — Mintz Levin Cohn Ferris Glovsky and Popeo, P.C.; Peter F. Corless; Steven M. Jensen

(57) ABSTRACT

A device and method for detecting crystal quality of a low temperature poly-silicon (LTPS) backplane are provided, the method including: projecting narrowband light to the LTPS backplane; performing image capturing of each position on a surface of the LTPS backplane at a first angle in a first axial direction to obtain a first diffraction image, the first angle being an angle of maximum diffraction light intensity in the first axial direction; performing another image capturing of each position on the surface of the LTPS backplane at a second angle in a second axial direction to obtain a second diffraction image, the second angle being an angle of maximum diffraction light intensity in the second axial direction; and determining the crystal quality of the LTPS backplane based on a diffraction light intensity distribution obtained from the first and second diffraction images.

23 Claims, 6 Drawing Sheets

(51) Int. Cl.
*G01N 21/47* (2006.01)
*G01N 21/95* (2006.01)

(56) References Cited

U.S. PATENT DOCUMENTS

| | | |
|---|---|---|
| 7,505,155 B2 | 3/2009 | Jang et al. |
| 2003/0017658 A1 | 1/2003 | Nishitani et al. |
| 2005/0002016 A1 | 1/2005 | Tsao |
| 2005/0189329 A1* | 9/2005 | Talwar ............... B23K 26/0604 219/121.65 |
| 2012/0057148 A1 | 3/2012 | Voronov et al. |
| 2013/0341310 A1 | 12/2013 | Van Der Wilt |

FOREIGN PATENT DOCUMENTS

| | | |
|---|---|---|
| TW | 201216393 A | 4/2012 |
| TW | 201248692 A | 12/2012 |
| TW | 201447273 A | 12/2014 |

\* cited by examiner

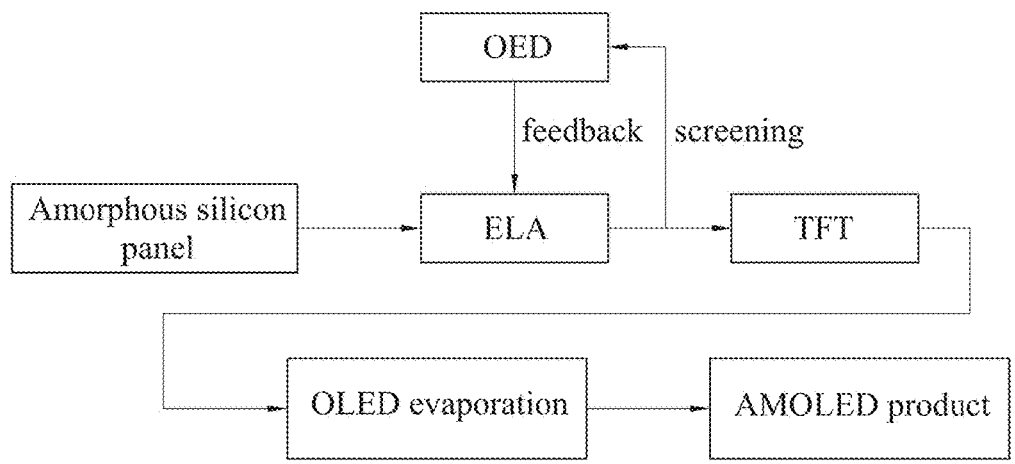
FIG. 1
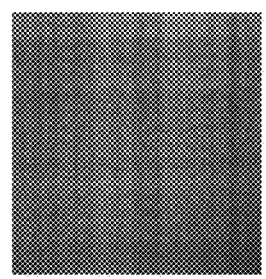 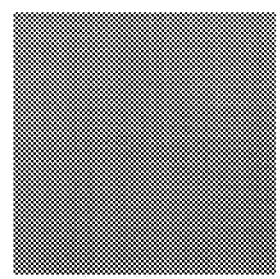
FIG. 2A   FIG. 2B

QUALITY DETECTING DEVICE AND METHOD

CROSS-REFERENCE TO RELATED APPLICATION

The present disclosure is based on, and claims priority from Taiwan Application Number 105137828, filed on Nov. 18, 2016, the disclosure of which is hereby incorporated by reference herein in its entirety.

TECHNICAL FIELD

The present disclosure relates to quality detecting technology for crystal quality of a Low Temperature Poly-silicon backplane.

BACKGROUND

An Active-Matrix Organic Light-Emitting Display (AMOLED) has gradually become the mainstream of the smart phone panel, and the focus for the national panel industry R & D as well as the technological breakthrough. Currently, in the AMOLED industry, the yield thereof is the biggest problem because low yield leads to more production and higher cost. Thus, for most of the panel makers in terms of AMOLED production yield, there is still an urgent need for improvement.

The AMOLED is mainly composed of a drive substrate, an OLED light-emitting layer and a cover. Although the drive substrate can be produced through plural technics, the Low Temperature Poly-silicon (LTPS) is still the mainstream. In the current AMOLED process, the quality of the LTPS process is one of the main phases that affect the yield of AMOLED. FIG. 1 exemplarily shows the AMOLED manufacturing process. The LTPS process includes the formation of the poly-silicon made from an amorphous silicon material by, for example, excimer-laser annealing (ELA). In general, after annealing, the crystal grains in the LTPS are periodically arranged in a regular arrangement, which looks similar to a grating. Nevertheless, if the quality of the LTPS backplane is poor, the linear defects occurs thereon, i.e., dislocations occur in parts of the regularly arranged crystal grains, as shown in FIG. 2A. This would cause the problem of luminance unevenness (Mura) to an AMOLED product, e.g., a display, as shown in FIG. 2B.

Moreover, the LTPS waste costs only about 1% of AMOLED products, for example, LTPS backplane costs about a few hundred dollars for each, but the AMOLED products costs about tens of thousands dollars for each. Accordingly, if the LTPS of poor quality (i.e., the defective LTPS) is screened out after laser annealing and before the AMOLED process, the chance of becoming an AMOLED waste can be reduced, and this helps to improve the process yield.

SUMMARY

According to an embodiment, a quality detecting device for detecting the crystal quality of an LTPS backplane is provided. The device includes a light source providing narrowband light to the LTPS backplane; a detector performing image capturing of each position on a surface of the LTPS backplane in a first axial direction at a first angle and in a second axial direction at a second angle, wherein the first image capturing is an angle of the maximum diffraction light intensity in the first axial direction, and the second angle is an angle of the maximum diffraction light intensity in the second axial direction; a carrier stage carrying the LTPS backplane and allowing the detector to capture a first diffraction image at the first angle in the first axial direction, and to capture a second diffraction image at the second angle in the second axial direction; and a processor determining the crystal quality of the LTPS backplane based on a diffraction light intensity distribution obtained from the first diffraction image and the second diffraction image.

According to an embodiment, a quality detecting method for detecting the crystal quality of an LTPS backplane is provided. The method includes the steps of: providing narrowband light to an LTPS backplane; performing image capturing of each position on a surface of an LTPS backplane at a first angle in a first axial direction to obtain a first diffraction image, the first angle being an angle of maximum diffraction light intensity in the first axial direction; performing another image capturing of each position on the surface of the LTPS backplane at a second angle in a second axial direction to obtain a second diffraction image, the second angle being an angle of maximum diffraction light intensity in the second axial direction; and determining crystal quality of the LTPS backplane based on a diffraction light intensity distribution obtained from the first diffraction image and the second diffraction image.

BRIEF DESCRIPTION OF THE DRAWINGS

FIG. 1 illustrates an AMOLED manufacturing process;

FIGS. 2A and 2B are photographs showing LTPS backplane defects as well as common luminance unevenness defects of the AMOLED products;

DETAILED DESCRIPTION OF DISCLOSED EMBODIMENTS

The following specific aspects of examples are for purposes of explanation to technical contents of the present disclosure. Further, a person skilled in the art can easily conceive advantages and effects recited in the present disclosure based on the contents thereof. Also, the present disclosure may be practiced or applied with other specific aspect of examples.

With regard to the LTPS crystal quality measurement, since the LTPS backplane shows as a yellow glass in the visible light, it is not easy to see anything therein with a conventional optical microscope testing machine. In this regard, based on the periodic arrangement property of the LTPS grains, occurrence of dislocations would cause defects in the display panel using LTPS. Accordingly, examples of the present disclosure use narrowband light to be incident on a surface of the LTPS backplane, and detect arrangement of the LTPS grain by analyzing the diffraction light produced thereby.

Figure 3:
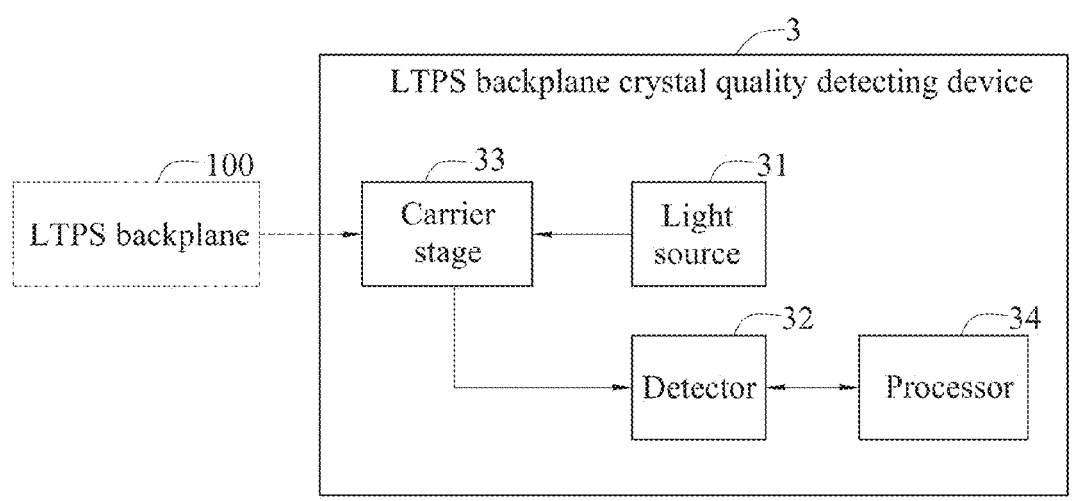
FIG. 3 is a system schematic view of an LTPS backplane crystal quality detecting device according to an embodiment.

FIG. 3 is a system schematic view of an LTPS backplane crystal quality detecting device 3 according to an embodiment. The LTPS backplane crystal quality detecting device 3 includes a light source 31, a detector 32, a carrier stage 33, and a processor 34.

The light source 31 provides narrowband light projecting to the LTPS backplane 100 on the carrier stage 33. The narrowband light is incident on the LTPS backplane 100, and thus diffraction light is produced due to crystal period arrangement of the LTPS backplane 100.

In an embodiment, the narrowband light may be LED light, laser light, halogen lamp plus filter or a light source plus filter, and a spectral full width at half maximum of the narrowband light may be 100 nm or less. In another embodiment, the spectral full width at half maximum of the narrowband light may be 10 nm or less.

A detector 32 performs an image capturing of each position on a surface of an LTPS backplane 100 at a first angle in a first axial direction, and a second angle in a second axial direction. In an embodiment, the first angle is an angle of the maximum diffraction light intensity in the first axial direction, and the second angle is an angle of the maximum diffraction light intensity in the second axial direction. In an embodiment, the detector 32 performs an image capturing of each position on a surface of an LTPS backplane at a first angle in the first axial direction to obtain a first diffraction image, and performs another image capturing of each position on the surface of the LTPS backplane at the second angle in the second axial direction.

The detector 32 detects a change in the light intensity of the diffraction light so as to determine an angle value of the maximum diffraction light intensity. Accordingly, the angle of the maximum diffraction light intensity becomes the first angle or second angle. When detecting the change in the light intensity of the diffraction light, the detector 32 performs a scanning detection in space. In an embodiment, the light intensity of the diffraction light in the scanning direction is detected by circular scanning, with the irradiation point of the incident light projected to the LTPS backplane 100 as an axis, in a direction of a parallel light incident surface.

In an embodiment, the light source 31 is fixed and the narrowband light is provided by the light source 31, which is incident on the LTPS backplane 100 to produce diffraction light. The detector 32 obtains an initial angle, i.e., a reflected angle, from a diffraction formula, and performs a scan of an angle value of the maximum diffraction light intensity at the initial angle. In an embodiment, the light is firstly to be found out, and a scan within a scope of about 10 degrees of the light is to be performed. Then, a scan with an angle of 5 degrees more is performed again so as to gradually approach an angle of the maximum diffraction intensity by such as the Newton method.

In an embodiment, the detector 32 is a line-scan image sensor. When intending to find out the maximum diffraction light intensity, the detector 32 may also be collated with an area-scan image sensor to assist the scanning. In an embodiment, the line-scan image sensor and area-scan image sensor may move synchronously. Due to a narrower sensing line width of the line-scan image sensor, a sensor signal may be unable or uneasy to be resolved if a sensing angle just falls right on a defect. Accordingly, collation of an area-scan image sensor may avoid or reduce an influence caused by a local defect. The area-scan image sensor may perform a light intensity scan of a two-dimensional region, and obtains an average value from the resulting results to reduce the influence of the local defect. After that, the light intensity is calculated based on all of the regions, and a certain region is then selected. Thus, the region is scanned with the line-scan image sensor to determine an angle value of the maximum diffraction light intensity.

Further, after determining an angle value of the maximum diffraction light intensity, the detector 32 selects the angle of the maximum diffraction light intensity as an angle, i.e., the first angle and the second angle. Then, the image capturing of each position on the surface of the LTPS backplane 100 is performed so as to obtain a diffraction light intensity distribution. As described above, the light source 31 and the detector 32 may no longer be changed once the angle value of the maximum diffraction light intensity is determined. The detector 32 may select the angle of the maximum diffraction light intensity in different axial directions as the angle so as to obtain a diffraction light intensity distribution on the surface of the LTPS backplane 100 of each position in different axial directions.

The carrier stage 33 may carry the LTPS backplane 100, allowing the detector 32 to capture a diffraction image at a first angle in a first axial direction, and to capture a second diffraction image at the second angle in a second axial direction. As described above, since the arrangement period of the LTPS grains produced after the laser annealing process may be different in different axial directions, crystal quality in one direction may be measured as good, but not the one measured in other axial directions. Accordingly, determination of crystal quality analyzed based on diffraction images in at least two axial directions would be more accurate.

In an embodiment, based on the diffraction light intensity distribution obtained from diffraction images in only one axial direction, the determination of the crystal quality may not be accurate enough. Therefore, the present disclosure provides a method of capturing images of the LTPS backplane 100 in different axial directions. The carrier stage 33 allows the detector 32 to capture images in different axial directions by, for example, rotating the carrier stage 33 that carries the LTPS backplane 100, changing the detectors 32 to be in different axial directions, and using a plurality of the detectors 32 in at least two different direction, such that the detector 32 may capture images of the LTPS backplane 100 in different axial directions.

Before the images in each axial direction are captured, the scanning of the angle of the maximum diffraction light intensity may be performed. Wavelengths of the narrowband light in different axial directions may be different. Owing to the shorter wavelength of the incident light (for example, a blue waveband), specific grain size would be shielded if unit grain size is too small. Accordingly, some defects cannot be detected by the blue light. Nevertheless, this problem may be solved by using the incident light having longer wavelength (e.g., a green waveband). Thus, in an embodiment, the scanning is performed with different wavelengths before determining the angle value of the maximum diffracted intensities in each axial direction. A diffraction intensity scanning is performed by using a first wavelength incident light with a detector in a first axial direction, and another diffraction intensity scanning is performed by using a second wavelength incident light with the detector in a second axial direction, wherein the first wavelength and the second wavelength may be different to each other, but the present disclosure is not limited thereto.

The diffraction angle may be calculated by the following equation: d (sin θi−sin θr)=mλ. Wherein d is an equivalent unit grain size, which is fixed after crystallization, and regarded as a mean value. However, since the value may be different in different axial directions, the wavelength may be changed for the scanning when changing to different axial directions. In addition, θi is an incident angle, θr is a diffraction angle, λ is a wavelength of a light source, and m is a non-zero integer. Once θi and λ are selected, a corresponding diffraction angle θr may be determined.

After rotating to other axial directions, the scanning of an angle value of the maximum diffraction light intensity and the capturing of a diffraction intensity distribution image of each position on the surface of the LTPS backplane 100 are performed. That is, treatment procedures are similar in each axial direction.

Then, based on a diffraction light intensity distribution obtained from the first diffraction image and the second diffraction image, the processor 34 determines the crystal quality of the LTPS backplane 100. As described above, by changing the axial direction to capture images of LTPS backplane, the detector 32 may perform the image capturing of various positions on the surface of the LTPS backplane 100 in different axial directions, so as to obtain the diffraction light intensity distribution. The processor 34 may integrate these diffraction light intensity distributions to give a score for the crystal quality of the LTPS backplane 100.

The score of the crystal quality of the LTPS backplane 100 may determine the quality of different manufacturing processing. For example, in an embodiment, two orthogonal axial directions are exemplified, and the detectors 32 capture diffraction light intensity distributions in the two orthogonal directions. Further, the processor 34 may combine images from the two directions with a specific weight ratio to calculate a score for evaluation. In an embodiment, with a weight ratio of 1:1, the score of the first axial direction is added to the score of the second axial direction, and then divided by two, wherein a higher score indicates a better crystal quality.

The weight ratio of 1:1 is used here because the LTPS backplane 100 would eventually be applied to the display. Preferably, pixels in the two axial directions should be as similar as possible, i.e., for fewer defects, the LTPS backplane 100 grain size corresponding to the display should be as similar as possible. In other words, if the grain size is identical, brightness of the display would be the same when being powered on. Accordingly, in terms of impact for crystallization, the two axial directions are equally important, and the weight ratio of 1:1 may be considered for calculation. However, the weight ratio is only one embodiment, and the present disclosure is not limited thereto.

Moreover, the detector 32 may be a line-scan image sensor or an area-scan image sensor. In an embodiment, if the light source 31 gives a narrowband light of a linear pattern, the detector 32 may be a line-scan image sensor. In another embodiment, if the light source 31 is a narrowband light providing a planar pattern, the detector 32 may be an area-scan image sensor. Certainly, there may be differences during the capturing by the line-scan image sensor or area-scan image sensor. This is to be described with examples later.

Given the foregoing, the present disclosure proposes use of the periodic arrangement property of the crystal grain, by which the diffraction light is produced when narrowband light is incident on the surface of the LTPS backplane, and the detector 32 detects the intensity of the diffraction light to obtain the angle of the maximum diffraction light intensity in each axial direction. Due to that the LTPS annealing process often causes grain arrangement periods of two axial directions to be different, diffraction conditions of the LTPS backplane in different axial directions for measurement may be different, and may be met by changing positions of the device.

In an embodiment, an angle for detection may be changed with the direction of the diffraction light, i.e., the angle of the detector 32 is changed. Further, the detector 32 may be fixed, but to change the incident angle of the narrowband light instead. This may be adjusted based on needs for design. Moreover, diffraction images in different axial directions may be similar but still different. Accordingly, the present disclosure determines the crystal quality of the LTPS backplane 100, based on the diffraction intensity distribution images in at least two axial directions, to entirely present all of the defects on the LTPS backplane.

The processor 34 is an illustrative example, and variations and modifications are possible. In an embodiment, the processor 34 may be implemented in a variety of form factors, including desktop systems, laptop systems, server systems, tablets, smart phones or personal digital assistants, and so on. In another embodiment, other functionality not described above may be further included, e.g., wired and/or wireless network interfaces, media playing and/or recording capability, etc. In yet another embodiment, the processor 34 may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic-circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

Figure 4:
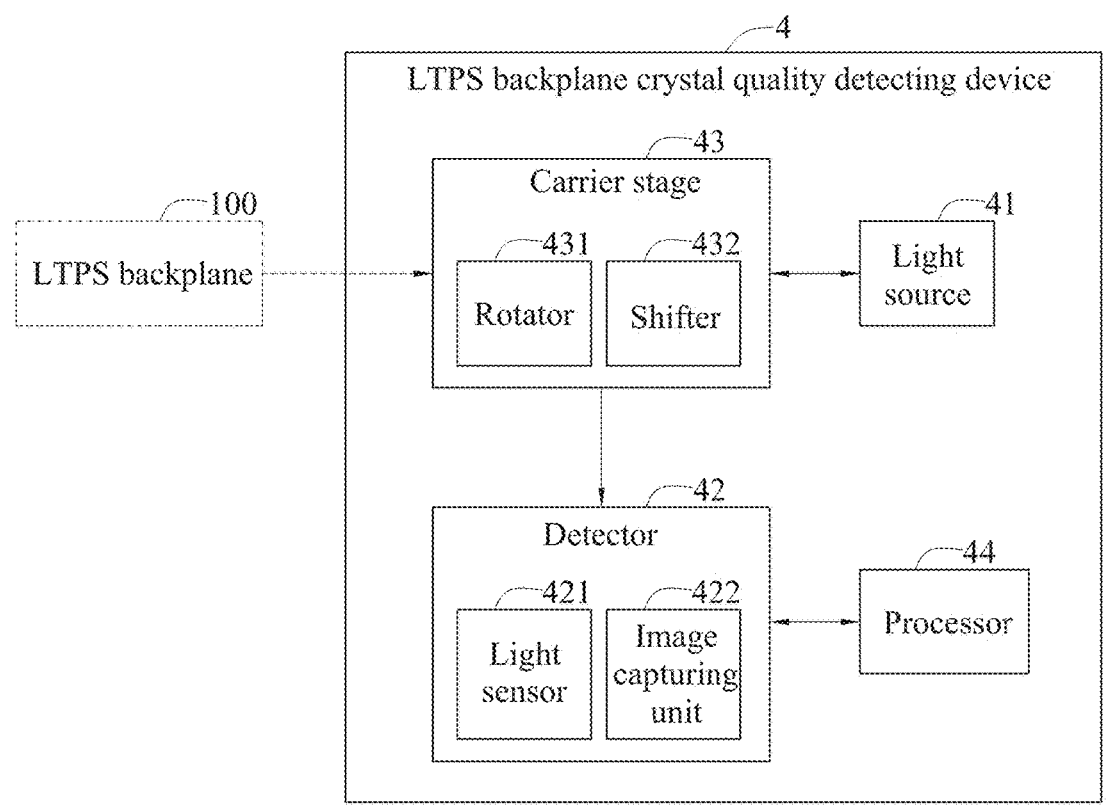
FIG. 4 is a system schematic view of an LTPS backplane crystal quality detecting device according to another embodiment.

FIG. 4 is a system schematic view of an LTPS backplane crystal quality detecting device according to another embodiment. The light source 41, the carrier stage 43, and the processor 44 of the LTPS backplane crystal quality detector 4 are the same as the light source 31, the carrier stage 33, and the processor 34 shown in FIG. 3, respectively. In an embodiment, the detector 42 may include a light sensor 421 and an image capturing unit 422, and the carrier stage 43 may include a rotator 431 and a shifter 432.

As described above, in addition to searching for an angle value of the maximum diffraction light intensity, the detector 42 may perform image capturing of each position on the surface of the LTPS backplane 100 after determining the angle value of the maximum diffraction light intensity. In an embodiment, the detector 42 includes a light sensor 421 for searching the angle value of the maximum diffraction light intensity and an image capturing unit 422 for capturing an image.

The light sensor 421 may be a light sensor for detecting a change in the light intensity of the diffraction light, which is supplied by the light source 41, and incident to the LTPS backplane 100. Owing to the LTPS backplane 100 grain period arrangement, the diffraction light is produced, the light sensor 421 may be used to sense the diffraction light, and the detector 42 performs the scanning of the diffraction light with the method as described above.

The image capturing unit 422 may be an image capturing device, e.g., a camera. The image capturing unit 422 may start an image capturing of each position on the surface of the LTPS backplane 100 after determining the angle value of the maximum diffraction light intensity. As described above, the detector 42 performs the scanning of the diffraction light with the method.

To provide image capturing in different axial directions and in a large area, the carrier stage 43 for carrying the LTPS backplane 100, by a rotator 431 and a shifter 432, allows the detector 42 to capture desired images from different axial directions or in a moving manner. In an embodiment, the carrier stage 43 may include a holding stage for holding the LTPS backplane 100, and a rotating motor (e.g., the rotator 431) or a shifting motor (e.g., the shifter 432) for changing a relative orientation or distance between the LTPS backplane 100 and the detector 42, but the disclosure is not limited thereto.

The rotator 431 is used to control rotation of the carrier stage 43, such that the detector 42 may perform image capturing of the LTPS backplane 100 in different axial directions. In an embodiment, with rotating the carrier stage 43 by an angle, e.g., 90 degrees, the detector 42 may perform image capturing in another axial direction orthogonal to the previous axial direction, but the disclosure is not limited thereto. As the detector 42 is fixed, the LTPS backplane 100, disposed on the carrier stage 43, is rotated by the rotator 431, such that the detector 42 captures images of the LTPS backplane 100 in different axial directions.

The shifter 432 is used to control movement of the carrier stage 43, such that the detector 42 may perform image capturing of each position on the surface of the LTPS backplane 100. In an embodiment, with moving the carrier stage 43 horizontally by, e.g., 0.1 cm, the detector 42 may perform image capturing of different positions in the same axial direction. The shifter 432 moves the LTPS backplane 100, such that the detector 42 captures images of different positions, without moving the detector 42, in the same axial direction as the LTPS backplane 100.

As described above, the detector 42 may be a line-scan image sensor or an area-scan image sensor. If the detector 42 is an area-scan image sensor, it may capture an image of the entire LTPS backplane 100 at one time without moving the LTPS backplane 100 by the shifter 432. If the detector 42 is a line-scan image sensor, the detector 42 may scan only one linear area at a time, i.e., without covering the entire LTPS backplane 100. Accordingly, when scanning or capturing image in the same axial direction, the shifter 432 moves the carrier stage 43 so as to horizontally displace the LTPS backplane 100, and the detector 42 may capture images of each position of the LTPS backplane 100.

Although the LTPS backplane 100 may be rotated, by the rotator 431, to capture images in different axial directions, this is simply in one embodiment. In another embodiment, changing positions of the detector 42 may bring about the same effect. That is, instead of rotating the LTPS backplane 100, the detector 42 is moved to an axial direction of images to be captured. As such, an effect of the image capturing in different axial directions may be achieved as well.

In an embodiment, the image capturing may be performed in two axial directions by the two detectors 42, respectively. In other words, the rotator 431 is not used to capture image in different axial directions, but the detectors 42 which are provided in each axial directions. The different detectors 42 are used to perform the image capturing in different axial directions. Therefore, setting up detectors in a plurality of axial directions and changing the axial direction may both achieve the image capturing in different axial directions, and may be adjusted based on needs as well.

All of the aforesaid examples are exemplified with the image capturing in the two axial directions. However, the present disclosure is not limited thereto. That is, the purpose for determining the LTPS backplane 100 crystal quality may also be achieved by capturing images in a plurality of axial directions. Specifically, the detector 42 performs image capturing of the LTPS backplane 100 in axial directions other than the original two axial directions, and the carrier stage 43 allows the detector 42 to capture other diffraction images in other axial directions. Also, the processor 44 determines the crystal quality of the LTPS backplane based on the diffraction light intensity distribution in each axial direction. It can be seen that the present disclosure, in order to determine the crystal quality, is not limited to diffraction image capturing only in two axial directions, but also in three or four axial directions. The diffraction light intensity distribution integrated from diffraction images in each direction may be used as a criterion for determination of the crystal quality.

Figure 5:
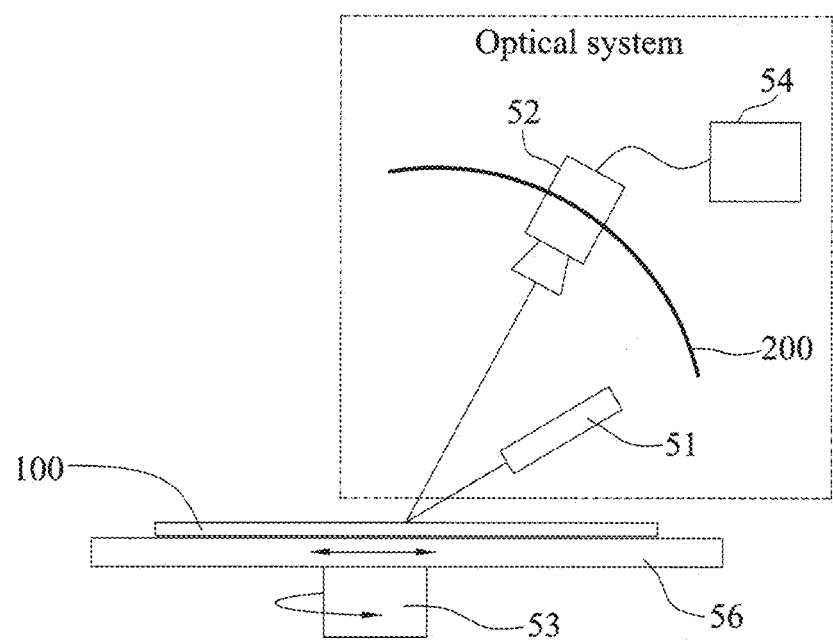
FIG. 5 is a schematic illustration of a specific embodiment of an LTPS backplane crystal quality detecting device according to an embodiment.

FIG. 5 shows a schematic view an LTPS backplane crystal quality detecting device according to an embodiment. The LTPS backplane crystal quality detecting device includes a carrier pedestal 56, and an optical system for optical scanning and image capturing, and this is a side view of the device. The carrier pedestal 56 is used for carrying the LTPS backplane 100. When the angle of the maximum diffraction light intensity is determined, a light source 51 is fixed and a detector 52 performs a scan with the light source 51 as an axis, i.e., to take the irradiation point as a center point, sliding in a slide track 200. After narrowband light providing from the light source 51 is projected to the LTPS backplane 100 to produce diffraction light, the detector 52 detects a change in the light intensity at each angle so as to determine the angle value of the maximum diffraction light intensity. The processor 54 may process calculation for this part.

Once the angle of the maximum diffraction light intensity is determined, a detector 52, which is also fixed, performs image capturing at this angle. If the detector 52 is a line-scan image sensor, the carrier pedestal 56 moves horizontally, such that the detector 52 may capture all images of each position of the LTPS backplane 100 in the same axial direction. Provided that the detector 52 is an area-scan image sensor, the detector 52 may, without moving the carrier pedestal 56, capture all images of the LTPS backplane 100 at one time.

In an embodiment, a rotator 53 rotates the carrier pedestal 56, allowing the detector 52 to capture images of the LTPS backplane 100 in different axial directions. Before images are captured, performing a scan for the angle of the maximum diffraction light intensity is necessary as well.

Figure 6A:
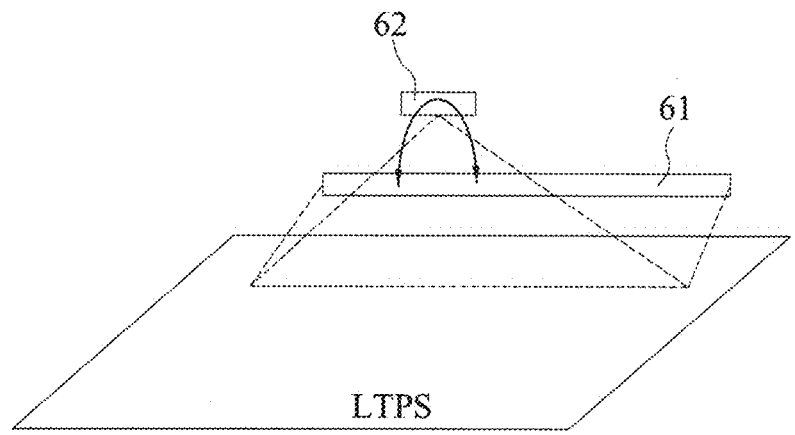
FIGS. 6A and 6B are schematic perspective views of an LTPS backplane crystal quality detecting device according to another two embodiments.
Figure 6B:
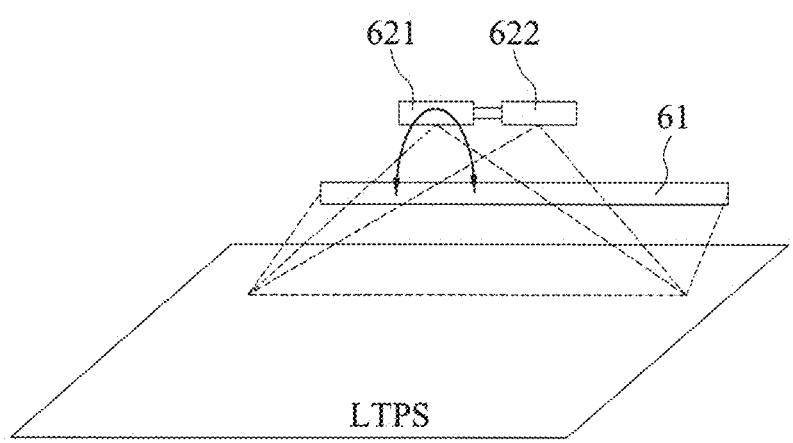

FIGS. 6A and 6B are schematic perspective views of the LTPS backplane crystal quality detecting device according to another two embodiments. In an embodiment, a narrowband light source of a linear pattern, or of a plurality of different wavelengths, may be used to be incident parallel to the surface of the LTPS backplane. Similarly, the diffraction light may be detected by using a linear arranged detector at a specific angle, i.e., the angle of the maximum diffraction light intensity, so as to detect diffraction signals of LTPS backplane in a linear range.

As shown in FIG. 6A, a light source 61 may provide a narrowband light source of a linear pattern. Also, a detector 62 also uses a linear arranged detector to receive diffraction light. As described above, when performing a scan for the angle value of the maximum diffraction light intensity, the detector 62 may slide in a track when performing the scan for detection of an angle.

As shown in FIG. 6B, the detector may be designed to include a light sensor 621 and an image capturing unit 622.

The light source 61 may provide a narrowband light source of a linear pattern, and the light sensor 621 may use a linear pattern detector to receive the diffraction light, which may slide in the track when scanning for the angle value of the maximum diffraction light intensity.

When the image capturing unit 622 is interlocked with the light sensor 621, i.e., when the light sensor 621 remains at a position of the maximum diffraction light intensity, the image capturing unit 622 also stays at the angle of the maximum diffraction light intensity, such that the image capturing unit 622 may perform the image capturing without adjusting the angle.

Figure 7:
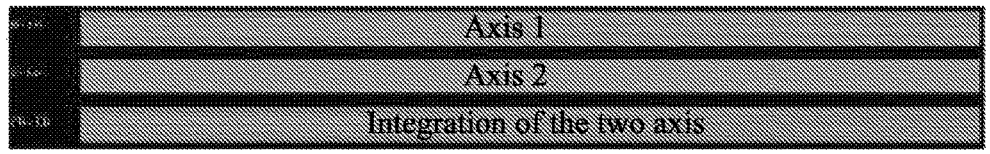
FIG. 7 is a photograph showing diffraction intensity distribution images in two axial directions of an LTPS backplane crystal quality detecting device according to an embodiment.

FIG. 7 shows a diffraction light intensity distribution of the LTPS backplane crystal quality detecting device in two axial directions according to one embodiment. The LTPS backplane crystal quality detecting device performs image capturing in two axial directions, so as to obtain a diffraction intensity distribution image of axis 1 and a diffraction intensity distribution image of axis 2. After integration with a weight ratio of, for example, 1:1, a diffraction light intensity distribution is obtained after integrating from the two axes. This fits the current criterion of manual inspection for the LTPS backplane quality.

Figure 8:
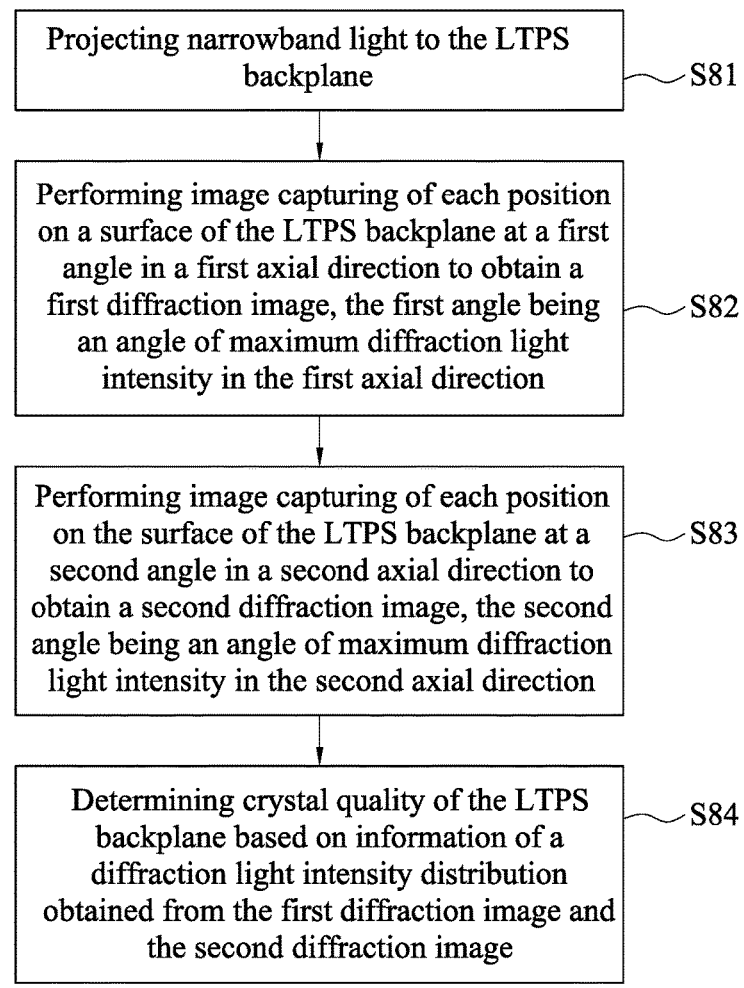
FIG. 8 is a flowchart illustrating steps of an LTPS backplane crystal quality detecting method according to an embodiment.

FIG. 8 is a flowchart illustrating the LTPS backplane crystal quality detecting method according to an embodiment. The LTPS backplane crystal quality detecting method finds out crystal defects on the LTPS backplane by a light diffraction method, and determines quality of the LTPS backplane by the following steps.

In step S81, narrowband light is projected to the LTPS backplane. In an embodiment, the narrowband light may be LED light, laser light or the like, and a spectral full width at half maximum thereof is 100 nm or less. In another embodiment, the spectral full width at half maximum of the narrowband light may be 10 nm or less.

In step S82, image capturing of each position on the surface of the LTPS backplane is performed in a first axial direction at a first angle to obtain a first diffraction image, and the first angle is an angle of the maximum diffraction light intensity in the first axial direction. Owing to the periodic arrangement of the LTPS backplane crystal grains, projecting narrowband light on the LTPS backplane causes production of diffraction light. That is, in step S82, the angle of the maximum diffraction light intensity in the first axial direction is determined, and then image capturing of each position on the surface of the LTPS backplane is performed to obtain an axial diffraction image.

Further, step S82 includes detecting a change in the light intensity of the diffraction light and finding an angle value of the maximum diffraction light intensity, so as to take the angle of the maximum diffraction light intensity as a first angle. Regarding the scanning of an angle value of the maximum diffraction light intensity, the angle value of the maximum diffraction light intensity can, by a Newton method, be approached in a specific range, i.e., an approximate angle obtained by a diffraction formula.

In an embodiment, after providing the narrowband light to the LTPS backplane, detecting the change in the light intensity of the produced diffraction light includes the scanning with the narrowband light as an axis to detect the change in the light intensity of the diffraction light. In other words, detecting the change in the light intensity of the diffraction light is performed by a circular-like scanning with an irradiation point of the incident light projected to the LTPS backplane 100 as an axis, but the present disclosure does not limit thereto.

In step S83, the image capturing of each position on the surface of the LTPS backplane is performed in a second axial direction at a second angle to obtain a second diffraction image, and the second angle is an angle of the maximum diffraction light intensity in the second axial direction. In step S83, after determining the angle of the maximum diffraction light intensity in the second axial direction, the image capturing of each position on the surface of the LTPS backplane is also performed at this angle to obtain the second diffracted image in the second axial direction.

As described above, since the produced arrangement period of the LTPS grains in different axial directions, after the laser annealing process, may not be the same, the crystal quality is thus determined based on values of a plurality of axial directions in this example.

In steps S82 and S83, before performing image capturing in the first axial direction and in the second axial direction, detecting a change in the light intensity of the diffraction light incident on the LTPS backplane by narrowband light is further included, so as to determine an angle value of the maximum diffraction light intensity. Thus, the angle of the maximum diffraction light intensity is the first angle or the second angle. That is, before the image capturing of each position on the surface of each LTPS backplane is performed, the angle value of the maximum diffraction light intensity in each axial direction is firstly determined.

Accordingly, once the angle of the maximum diffraction light intensity is determined, the angle of the maximum diffraction light intensity is taken as the angle for performing the capturing of the diffraction intensity distribution image of each position on the surface of the LTPS backplane.

The image capturing of each position on the surface of the LTPS backplane may be obtained by the line-scan image sensor or the area-scan image sensor. In case of the area-scan image sensor, a two-dimensional image of each position on the surface of the LTPS backplane may be obtained (or an overall two-dimensional image of the LTPS backplane). Nevertheless, in case of the line-scan image sensor, when performing the image capturing of each position on the surface of the LTPS backplane in the steps S82 and S83, rotating the LTPS Backplane from one axial direction to another axial direction is further included, so as to obtain the image capturing in different axial directions. Moreover, the LTPS backplane may be further moved, i.e., by the horizontal movement of the LTPS backplane, to capture the LTPS backplane overall image.

In step S84, the crystal quality of the LTPS backplane is determined based on the diffraction intensity distribution image of the first diffraction image and the second diffraction image. In this step, the diffraction light intensity distributions obtained from the two axial directions are integrated to determine the crystal quality of the LTPS backplane.

The crystal quality of LTPS backplane of different processes may be determined and given a different score for a level of the quality. In an embodiment, the diffraction light intensity distribution in each axial direction has a score. For example, scores of the images of the two orthogonal axial directions, with a weight ratio of 1:1, are added and divided by two. The higher the score is, the better the crystal quality is. In addition, the weight ratio may be adjusted based on needs or the number of axial directions.

In an embodiment, the LTPS backplane crystal quality detecting method may further include performing image capturing of the LTPS backplane in other axial directions, so as to determine the crystal quality of the LTPS backplane, based on the diffraction light intensity distribution in each axial direction. In short, the foregoing is determination of the crystal quality of the LTPS backplane based on the diffraction intensity distribution image in at least two axial directions. Nevertheless, the number of axial directions may be changed, for example, to three or four.

The aspects of the examples described above are only exemplified for illustration of the principles and effects of, but not used to limit, the present disclosure. Also, without departing from the spirit and scope of the present disclosure, modifications and variations can be made to the disclosed aspects of the examples as described above by a person skilled in the art. Hence, it is intended that a true scope of the present disclosure is set forth in the appended claims.

What is claimed is:

1. A quality detecting device, comprising:
a light source configured to provide a narrowband light projecting to an low temperature poly-silicon (LTPS) backplane, the narrowband light, after being projected to the LTPS backplane, producing diffraction light;
a detector configured to perform image capturing of each position on a surface of the LTPS backplane in a first axial direction at a first angle and in a second axial direction at a second angle, wherein the first angle is an angle of maximum diffraction light intensity in the first axial direction, and the second angle is an angle of maximum diffraction light intensity in the second axial direction;
a carrier stage configured to carry the LTPS backplane and allow the detector to capture a first diffraction image at the first angle in the first axial direction and a second diffraction image at the second angle in the second axial direction; and
a processor configured to determine crystal quality of the LTPS backplane based on a diffraction light intensity distribution obtained from the first diffraction image and the second diffraction image.

2. The device of claim 1, wherein the detector is configured to detect a change in light intensity of the diffraction light so as to determine an angle of the maximum diffraction light intensity, and the angle of the maximum diffraction light intensity is used as the first angle or the second angle.

3. The device of claim 2, wherein the detector is configured to perform a scan capturing to the surface of the LTPS backplane so as to detect the change in the light intensity of the diffraction light.

4. The device of claim 1, wherein the detector includes:
a light sensor configured to determine an angle of the maximum diffraction light intensity; and
an image capturing unit configured to capture an image.

5. The device of claim 1, wherein the detector is a line-scan image sensor or an area-scan image sensor.

6. The device of claim 1, wherein the carrier stage comprises a rotator configured to control rotation of the carrier stage, allowing the detector to perform an image capturing of the LTPS backplane in multiple axial directions.

7. The device of claim 1, wherein the carrier stage comprises a shifter configured to control a movement of the carrier stage, allowing the detector to perform an image capturing of each position on a surface of the LTPS backplane.

8. The device of claim 1, wherein the performance of the image capturing in the first axial direction and the second axial direction comprises two detectors performing an image capturing in the first axial direction and in the second axial direction, respectively.

9. The device of claim 1, wherein a spectral full width at half maximum of the narrowband light is 100 nm or less.

10. The device of claim 9, wherein the spectral full width at half maximum of the narrowband light is 10 nm or less.

11. The device of claim 1, wherein the first axial direction is orthogonal to the second axial direction.

12. The device of claim 1, wherein the detector is further configured to perform an image capturing of the LTPS backplane in another axial direction, and the processor is configured to determine the crystal quality of the LTPS backplane based on the diffraction light intensity distribution in each axial direction.

13. An method for detecting crystal quality of an LTPS backplane, comprising:
projecting narrowband light to the LTPS backplane;
performing image capturing of each position on a surface of the LTPS backplane at a first angle in a first axial direction to obtain a first diffraction image, the first angle being an angle of maximum diffraction light intensity in the first axial direction;
performing image capturing of each position on the surface of the LTPS backplane at a second angle in a second axial direction to obtain a second diffraction image, the second angle being an angle of maximum diffraction light intensity in the second axial direction; and
determining crystal quality of the LTPS backplane based on information of a diffraction light intensity distribution obtained from the first diffraction image and the second diffraction image.

14. The method of claim 13, further comprising:
prior to performing the image capturing in the first axial direction or in the second axial direction, detecting a change in the light intensity of diffraction light, so as to determine an angle of maximum diffraction light intensity, wherein the angle of the maximum diffraction light intensity is used as the first angle or the second angle.

15. The method of claim 14, wherein the step of detecting the change in the light intensity of the diffraction light includes performing scan capturing to the surface of the LTPS backplane so as to detect the change in the light intensity of the diffraction light.

16. The method of claim 13, wherein the step of performing the image capturing of each position on the surface of the LTPS backplane is performed through a line-scan image capturing or an area-scan image capturing.

17. The method of claim 13, wherein the step of performing the image capturing in the first axial direction and in the second axial direction includes rotating the LTPS backplane from the first axial direction to the second axial direction.

18. The method of claim 13, wherein the step of performing the image capturing of each position on the surface of the LTPS backplane further includes moving the LTPS backplane.

19. The method of claim 13, wherein the step of performing the image capturing in the first axial direction and in the second axial direction includes performing the image capturing in the first axial direction and in the second axial direction, respectively, without the LTPS backplane rotated.

20. The method of claim 13, wherein a spectral full width at half maximum of the narrowband light is 100 nm or less.

21. The method of claim 20, wherein the spectral full width at half maximum of the narrowband light is 10 nm or less.

22. The method of claim 13, wherein the first axial direction is orthogonal to the second axial direction.

23. The method of claim 13, further comprising performing the image capturing of the LTPS backplane in another axial direction, so as to determine the crystal quality of the LTPS backplane in accordance with the diffraction light intensity distribution in each axial direction.

* * * * *